United States Patent
Viviers et al.

(10) Patent No.: US 10,302,637 B2
(45) Date of Patent: May 28, 2019

(54) DEVICE FOR DETECTING TARGET BIOMOLECULES

(71) Applicant: Stellenbosch University, Stellenbosch (ZA)

(72) Inventors: Christiaan Gunter Alwyn Viviers, Stellenbosch (ZA); Willem Jacobus Perold, Somerset West (ZA); Leon Milner Theodore Dicks, Stellenbosch (ZA); Giles Hubert Coyle Maybery, Port Elizabeth (ZA)

(73) Assignee: Stellenbosch University, Stellenbosch (ZA)

( * ) Notice: Subject to any disclaimer, the term of this patent is extended or adjusted under 35 U.S.C. 154(b) by 77 days.

(21) Appl. No.: 15/352,690

(22) Filed: Nov. 16, 2016

(65) Prior Publication Data

US 2017/0138934 A1 May 18, 2017

(30) Foreign Application Priority Data

Nov. 18, 2015 (ZA) .................................. 2015/08499

(51) Int. Cl.
*G01N 33/553* (2006.01)
*G01N 33/543* (2006.01)
*G01N 27/12* (2006.01)
*G01N 33/573* (2006.01)

(52) U.S. Cl.
CPC ....... *G01N 33/5438* (2013.01); *G01N 27/125* (2013.01); *G01N 33/553* (2013.01); *G01N 33/573* (2013.01); *G01N 2333/936* (2013.01); *G01N 2469/20* (2013.01)

(58) Field of Classification Search
None
See application file for complete search history.

(56) References Cited

U.S. PATENT DOCUMENTS

| 4,956,275 | A | * | 9/1990 | Zuk | .................. | G01N 33/54386 |
| | | | | | | 435/25 |
| 5,753,519 | A | * | 5/1998 | Durst | ............... | G01N 33/54313 |
| | | | | | | 204/288 |
| 7,674,616 | B2 | * | 3/2010 | Farnam, III | ............. | C12Q 1/56 |
| | | | | | | 422/50 |
| 2002/0150886 | A1 | | 10/2002 | Miles et al. | | |
| 2007/0037153 | A1 | | 2/2007 | Mandrand et al. | | |
| 2015/0309024 | A1 | | 10/2015 | Demirci et al. | | |

FOREIGN PATENT DOCUMENTS

WO 2010003212 A1 1/2010

OTHER PUBLICATIONS

McGraw, et al., "A Resistance Based Biosensor that Utilizes Conductive Microfthers for Microbial Pathogen Detection", Open Journal of Applied Biosensor, 2012, 1, pp. 36-43.

* cited by examiner

*Primary Examiner* — Christopher L Chin
(74) *Attorney, Agent, or Firm* — Banner & Witcoff, Ltd.

(57) ABSTRACT

A device for detecting target biomolecules is provided. The device consists of an electrically conductive membrane having a biological recognition component configured to bind a target biomolecule immobilized thereon. The membrane is connected to an electric circuit by means of electrodes. A voltage source applies a voltage to the membrane and a resistance monitoring device monitors the resistance of the membrane as a selected volume of fluid sample suspected of containing the target biomolecule is delivered onto the membrane.

19 Claims, 9 Drawing Sheets

DEVICE FOR DETECTING TARGET BIOMOLECULES

CROSS-REFERENCE TO RELATED APPLICATIONS

This application claims priority from South African provisional patent application number 2015/08499 filed on 18 Nov. 2015, which is incorporated by reference herein.

FIELD OF THE INVENTION

This invention relates to a device for detecting target biomolecules. In particular, it relates to a device for detecting target biomolecules by measuring a change in conductivity of an electrically conductive membrane to which a biological recognition component configured to bind the target biomolecule is attached.

BACKGROUND TO THE INVENTION

The early diagnosis of pathogenic infections may help reduce the number of incidents of disease and fatalities caused by pathogenic infections in humans. Infections may be further reduced by the detection of pathogenic agents in water or food before consumption. Traditional pathogen detection methods such as polymerase chain reaction, immunology-based methods and culture and colony counting generally take a long time to provide accurate results and can be expensive and inaccessible in remote locations. To address this problem, a variety of biosensors that detect biomolecules for diagnostic or quality control purposes have been developed.

Electrochemical biosensors are sensors used to detect target biomolecules suspended in a solution by means of molecular recognition. A typical electrochemical biosensor includes at least one electrode with biological recognition components immobilized on the surface of the electrode which are able to bind to or complex with target biomolecules in the solution. The biological recognition components may be pathogens or antigens, antibodies, enzymes or nucleic acids for example. The biosensors are configured to measure changes in the conductivity of the electrode due to the binding or complexation of biomolecules from a solution to the biological recognition components immobilized on the electrode. In effect, changes in the resistance of the electrode when connected in an electric circuit to which a constant potential difference and current is applied, is measured.

Recent developments in the field of electrochemical biosensing have resulted in the use of so-called "electrotextiles", which are membranes that consist of polymer fibers that have been coated with a conductive polymer coating, as the electrode. The microfibers provide a large surface area for the immobilization of a substantial amount of the biological recognition components on the surface of the electrode.

The applicant is aware of a laboratory-scale system in which an electrotextile is submerged in a buffer solution and connected to a circuit by means conductive metal clips that serve as electrodes. Both the electrotextile and clips are submerged in a solution containing sodium chloride, potassium chloride, sodium phosphate and potassium phosphate salts. The sample solution containing biomolecules to be detected is then added to the buffer solution and changes in the conductivity of the electrotextile after addition of the sample solution is measured. However, the submerged electrodes participate in electrochemical reactions with the salts in the solution, producing a substantial background effects during the detection process which reduces the sensitivity of the system. As a result of being submerged in a saline solution, the electrodes are also susceptible to degradation over time caused by redox reactions on the surface of the electrodes. The system also needs a relatively large volume of buffer solution, which may not be readily available outside of a laboratory environment.

In general, existing systems that utilize electrotextiles for the detection of biomolecules are complex, laboratory-scale systems that may not be suitable for use in the field or re-use and may not be sensitive enough to be used with very small fluid samples. There thus remains a need for a cost-effective, versatile, sensitive and robust device for detecting the presence of biomolecules. Ideally the device must be of a relatively simple construct and easy to use so that it may be utilized in the field in order to rapidly detect biomolecules linked to pathogenic infection or contamination.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with the invention there is provided a device for detecting target biomolecules comprising an electrically conductive membrane having a biological recognition component configured to bind a target biomolecule immobilized thereon, the membrane being connected to an electric circuit by means of electrodes; a voltage source for providing a voltage within the electric circuit; and a resistance monitoring device configured to monitor the resistance of the membrane as a selected volume of fluid sample is delivered onto the membrane.

Further features provide for the membrane to be mounted on a non-conducting support which is configured to releasably receive and hold the conductive membrane such that it contacts the electrodes; for the support to define a chamber that houses the membrane; for the electrodes to extend into the chamber to contact the membrane housed therein; for the support to include an inlet for the delivery of the selected volume of fluid sample onto the membrane; and for the selected volume of fluid sample to be between 10 and 1000 µl.

Yet further features provide for the membrane to be made of inherently electrically conductive fibers or polymer fibers coated with an electrically conductive coating; and for the electrically conductive coating to be a polymeric coating selected from the group consisting of polypyrrole, polythiophene, polyaniline and polyacetylene optionally including a dopant.

Still further features provide for the biological recognition component to be attached to the membrane by a cross-linking agent; and for the biological recognition component to be an antigen for operatively binding a target antibody or an antibody for operatively binding a target antigen.

Further features provide for the device to include a controller configured to issue machine-readable instructions to the voltage source to apply a voltage and being further configured to issue machine-readable instructions to the resistance monitoring device to monitor it and take readings of the resistance across the membrane; for the controller to be configured to issue machine-readable instructions to a signaling component that signals the detection of a target biomolecule if a resistance is measured by the resistance monitoring device that is above a predetermined threshold resistance which is a resistance of the membrane without a fluid sample delivered onto the membrane; for the controller to be configured to process the readings of the resistance across the membrane to quantify the amount of biomolecules in the sample and assign a level of contamination or infection to the fluid sample; and for the controller to have a user interface and display for displaying a signal, quantified amount of biomolecules and/or a level of contamination or infection.

A further feature provides for the resistance monitoring device to be a voltage measurement device connected across the membrane and for the resistance of the membrane to be determined from a voltage drop measured across the membrane.

Yet a further feature provides the device to be portable and battery-operated.

In accordance with a second aspect of the invention, there is provided a method of detecting a target biomolecule using the device described above and comprising the steps of:

delivering a selected volume of fluid sample onto an electrically conductive membrane on which a biological recognition component configured to bind a target biomolecule is immobilized;

monitoring the resistance of the membrane; and if the resistance is above a threshold resistance, signaling the detection of the target biomolecule.

An embodiment of the invention will now be described, by way of example only, with reference to the accompanying drawings.

DETAILED DESCRIPTION WITH REFERENCE TO THE DRAWINGS

Figure 1:
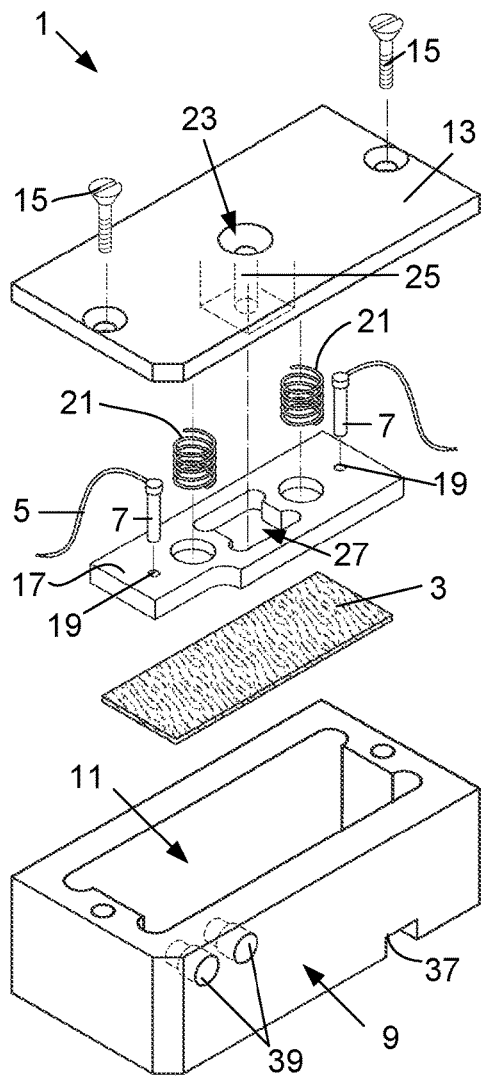
FIG. 1 is a three-dimensional exploded view of an embodiment of a device for detecting target biomolecules in accordance with the invention.
Figure 2:
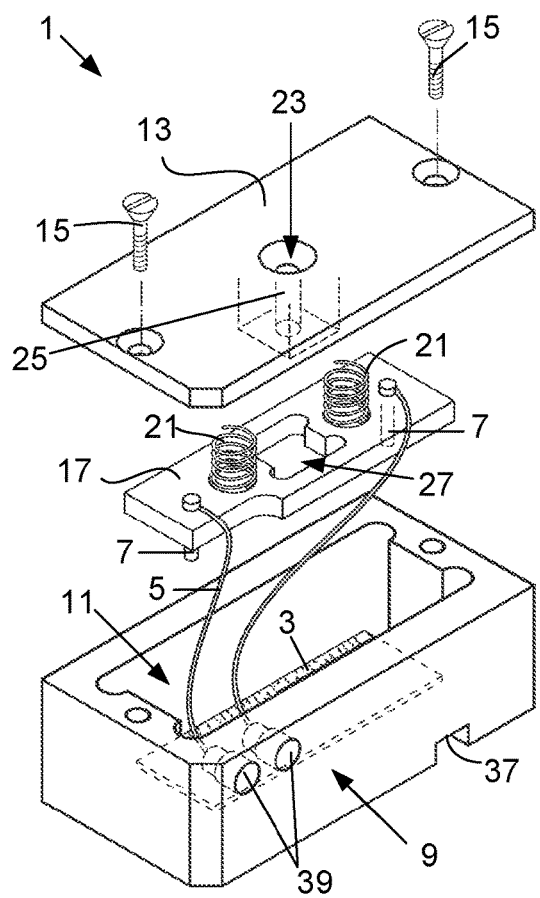
FIG. 2 is a three-dimensional exploded view of the embodiment of FIG. 1 with various components in their relative positions.
Figure 3:
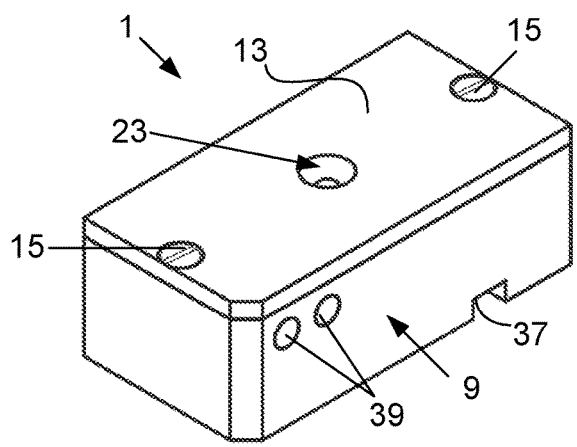
FIG. 3 is a three-dimensional view of the embodiment of FIG. 1 in an assembled condition.
Figure 4:
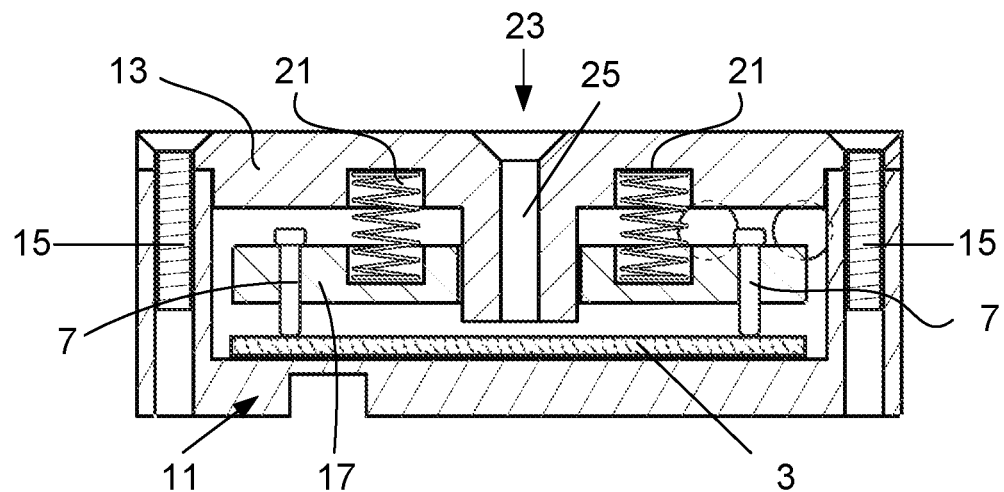
FIG. 4 is a cross-sectional view of the embodiment of FIG. 1 in an assembled condition.

The invention provides a device for detecting target biomolecules in a fluid using an electrically conductive membrane having a biological recognition component configured to bind a target biomolecule immobilized thereon. The membrane is connected to an electric circuit by means of electrodes made of a conductive metal such as gold, copper or platinum. A voltage source connected within the circuit provides a voltage to the membrane which is selected to be within a voltage range that generally does not cause denaturation or degradation of the biological recognition component immobilized on the membrane. A resistance monitoring device monitors the resistance of the membrane as a selected volume of fluid sample suspected of containing a biomolecule that is able to associate with the biological recognition component is delivered onto the membrane. The resistance monitoring device may be a voltage measurement device connected across the membrane. The resistance of the membrane is then determined from a voltage drop measured across the membrane.

The membrane is mounted on a non-conducting support. The support is configured to releasably receive and hold the conductive membrane such that it extends between the electrodes. The electrodes may be attached or adjustably secured to the support so as to extend from the support towards the membrane. The membrane may be sandwiched between the electrodes or between the electrodes and the support. The electrodes are suitably positioned to contact the membrane and may be biased to a position in which it contacts the membrane by suitable biasing means such as a spring. The support may define a chamber that houses the membrane to protect the membrane from the environment and provide a relatively constant testing environment therein. The electrodes then extend from the support and into the chamber where it contacts the membrane. If required, the support may include access ports for circuit wiring to extend through the support to the electrodes within the chamber.

The support may define an inlet for the delivery of the selected volume of fluid sample, preferably ranging between 10 and 1000 µl, preferably between 100 and 300 µl onto the membrane. The inlet may be positioned such that the selected volume of the fluid sample is delivered onto a central region of the membrane and may be positioned intermediate the electrodes along the length of the support.

The membrane may be made of inherently electrically conductive polymer fibers or fibers coated with an electrically conductive coating. The membrane may be formed of very fine, highly graphitic tubular carbon nanofibers that are heat treated to carbonize chemically vapor deposited carbon present on the surface of the nanofibers such as PYROGRAF®-III-LHT. Alternatively, the polymer fibers may be natural or synthetic fibers coated with an electrically conductive coating such as a polymeric coating selected from the group consisting of polypyrrole, polythiophene, polyaniline and polyacetylene. In the case of natural fibers, the membrane may be made of cellulosic fibers pressed into paper of a selected thickness that are coated with a conductive coating. Alternatively, synthetic polymer fibers of polypropylene may be coated with an electrically conductive coating.

The biological recognition component may be an antigen, antibody, enzyme, nucleic acid or other type of biomolecule. The biological recognition component is configured to be capable of binding to a target biomolecule. The biological recognition component thus has a binding site which is complementary to a binding site on the target biomolecule. For example the biological recognition component may be an antibody such as anti-$E.\ coli$ antigen which may operatively bind an antigen such as $E.\ coli$ bacteria to detect $E.\ coli$ contamination in a water sample. Alternatively the biological recognition component may be an antigen such as $E.\ coli$ that binds the anti-$E.\ coli$ antibody to detect an infection in an animal-derived fluid sample. In the event that the biological recognition component is a nucleic acid, it may be used to detect the presence of a target virus.

The biological recognition component is attached to the conductive membrane with a suitable linking agent. Any suitable linking agent may be used to link the biological recognition component to the membrane depending on the identity and nature of the biological recognition component and the membrane respectively. The linking agent should have the correct chemical functional groups to bind to both the conductive fibers via functional groups that may have been provided on the surface of the microfibers and to bind the selected biological recognition component, preferably by covalent bonds which provide a relatively strong linkage.

The device may include a controller configured to issue machine-readable instructions to the voltage source to apply a voltage and to issue machine-readable instructions to the resistance monitoring device to monitor it and take readings of the resistance across the membrane. The device may also include a signaling component, in which case the controller is also configured to issue machine-readable instructions to a signaling component that signals the detection of a target biomolecule if a resistance is measured by the voltage measurement device that is above a predetermined threshold resistance. The predetermined threshold resistance may be set to correspond to a resistance of the membrane without a fluid sample delivered onto the membrane; a resistance of the membrane with a control fluid containing substantially no biomolecules delivered onto the membrane; or a resistance of the membrane with a control fluid containing biomolecules that the biological recognition component will not recognize or bind to delivered onto the membrane. The device may include a second control membrane, the resistance of which is monitored and measured in order to determine the threshold resistance to be used to assess the change in resistance of the first membrane more accurately relative to that measured for the second membrane. The support may be suitably adapted to allow it to receive and hold the second membrane and to provide it a second set of electrodes and circuit wiring. The support may also include a second inlet for the delivery of a control solution onto the second membrane, if required.

The controller may be configured to process the readings of the resistance across the membrane to quantify the amount of biomolecules in the sample and assign a level of contamination or infection to the fluid sample. The controller may also include a user interface and display such as an LCD (LCM1602) display for displaying a signal, quantified amount of biomolecules and/or a level of contamination or infection.

The device may be a portable, point-of-care device which is powered by a portable power source such as batteries or solar panels. The power source may be configured to simultaneously provide the voltage to the electrodes connected to the membrane and to power the controller and resistance monitoring device.

An embodiment of a device (1) for the detection of biomolecules is show in FIGS. 1 to 5 and includes a generally rectangular conductive membrane (3) of about 30 mm×15 mm with a selected biological recognition component such as an antigen or antibody immobilized on its surface. In this embodiment, the membrane (3) is formed from polypropylene microfibers having a thickness of 50 g/m$^2$. The microfibers are arranged to form a nonwoven, spun bound and spot melted textile membrane. The microfibers of the membrane are substantially uniformly coated with a conductive coating, in particular a polymeric coating, using an aqueous deposition process. The conductive coating is a doped polypyrolle coating which is obtained by the copolymerisation of the membrane microfibers with a pyrrole monomer solution containing 3-thiopheneacetic acid (3TAA). The 3TAA ensures the inclusion of functional groups that can covalently link to cross-linking agents and/or directly to biological recognition components in order to immobilize the biological recognition components on the surface of the microfibers of the membrane. Following the copolymerisation, the microfibers are doped with a 5-sulfosalicylic acid in the presence of iron (III) chloride solution.

A cross-linking agent, in this embodiment glutaraldehyde, is used to bind the biological recognition component to the membrane. Glutaraldehyde is reactive towards amine groups which are commonly found on biomolecules such as proteins. The conductive membrane (3) onto which the biological recognition component is immobilized is connected to an electric circuit by means of electric wiring (5) connected to conductive electrodes (7). In this embodiment the electrodes are in the form of pins made of gold. The membrane (3) is received in a chamber (11) defined in a support (9). The chamber (11) is complementarily shaped to the membrane (3). The support (9) is made of a non-conductive material such as a plastics material. The support (9) includes a cover (13) which encloses the membrane (3) within the chamber (11). The cover (13) is secured to the open end of the chamber (11) using suitable fasteners or fastening means, in this embodiment screws (15).

The support (9) includes a mount (17) for the electrodes (7) configured to be received within the chamber (11). The mount has locating formations in the form of apertures (19) through which the electrodes (7) extend. The apertures (19) are spaced a selected distance apart in order to position the electrodes such that the membrane extends therebetween in an assembled condition. The mount (17) is biased toward the membrane (3) by biasing means in the form of springs (21) operable between the cover (13) and mount (17). The springs (21) operatively bias the electrodes toward the membrane in order to maintain contact between the electrodes (7) and the membrane (3) situated at the base of the chamber (11). The membrane (3) is held captive between the electrodes (7) and the base of the support (9). The electrodes (7) are arranged to apply more or less the same pressure to the membrane (3) to improve the accuracy of the readings of the resistance of the membrane (3).

The cover (13) of the support (9) further defines an inlet (23) for the delivery of fluid sample to a central region of the membrane in use. The inlet (23) is arranged to be intermediate the electrodes (7) along the length of the support (9). The cover (13) defines a channel (25) shown in broken lines in FIGS. 1 and 2 and most clearly shown in FIG. 4. The channel (25) directs the fluid sample onto the membrane (3) in use. The channel (25) extends through a window (27) in the mount (17) in the direction of the membrane (3) and terminates operatively above the membrane (3).

Figure 5:
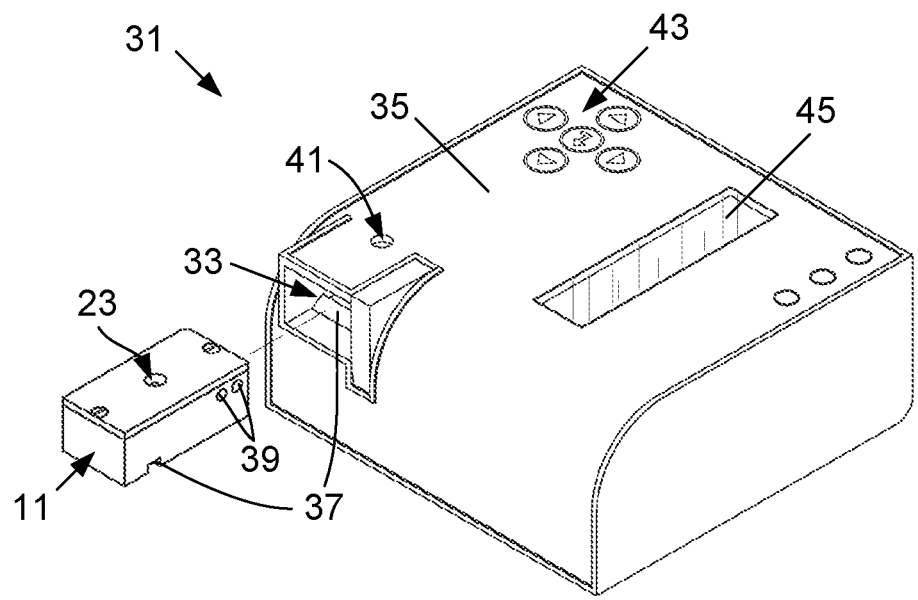
FIG. 5 is a three-dimensional view of the embodiment of FIG. 1 in an assembled condition and a controller.

An embodiment of a device (31) for detecting biomolecules including a controller is shown in FIG. 5. The support (9) containing the membrane and all assembled components shown in FIGS. 1 to 4 is inserted into a cavity (33) defined in the body of a portable computing device (35). Complementary locating formations (37) on the support (9) and the computing device (35) ensures the support (9) is held in place in the cavity (33). The body of the computing device includes an aperture (41) which aligns with the inlet (23) of the support (9) when the support is received within the cavity (33) for providing access to the inlet (23) to deliver a fluid sample to be tested through the aperture (41) and into the inlet (23) so that it can pass onto the membrane (3) in use.

The support (9) has two electrical contacts (39) arranged to ensure electrical communication between the electrodes and the resistance monitoring device such that the resistance of the membrane can be monitored and recorded.

The controller, preferably a microcontroller, is configured to issue machine-readable instructions to a voltage source to apply a voltage to the membrane and to issue machine-readable instructions to the resistance monitoring device to monitor it and take readings of the resistance across the membrane after the delivery of a selected volume of fluid sample to the membrane. The controller is further configured to process the readings of the resistance across the membrane to signal the presence of a biomolecules and/or quantify the amount of biomolecules in the sample and assign a level of contamination or infection to the fluid sample. The controller may also include a user interface (43) for user input. An LCD display (45) is provided for displaying a signal, quantified amount of biomolecules and/or a level of contamination or infection. In an alternative embodiment, the user interface may be configured to allow simultaneous user input and output. The embodiment of FIG. 5 finds use as a portable, point-of-care device for detecting target biomolecules and is powered by a battery. The device may be further configured to serially or wirelessly communicate with another device such as a personal computer or a smart phone.

Figure 6:
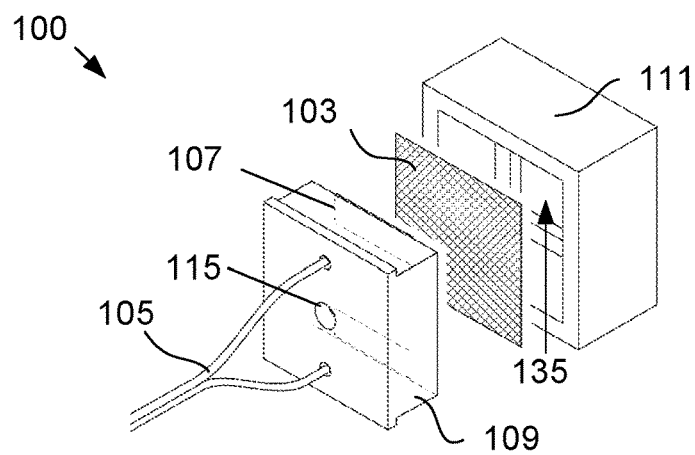
FIG. 6 is a three-dimensional exploded view of a further embodiment of a device for the detection of biomolecules.

A further embodiment of a device (100) for the detection of biomolecules is shown in FIGS. 6 to 9 and includes a generally square-shaped conductive membrane (103) of about 30×30 m having a selected biological recognition component immobilized thereon. The conductive membrane (103) onto which the biological recognition component is immobilized is connected to an electric circuit by means of electric wiring (105) connected to conductive electrodes (107) in the form of plates made of copper. The electrodes (107), shown in broken lines in FIG. 6, are spaced 17 mm apart and fixed to a support (109). A cover (111) cooperates with the support and the membrane (103) is held captive between the cover (111) and the electrodes (107) fixed to the support (109) when the support (109), membrane (103) and cover (111) are assembled.

Figure 7:
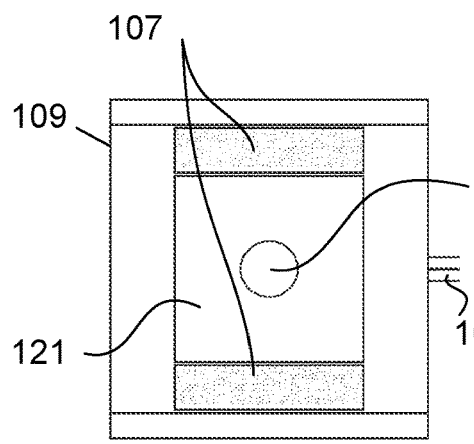
FIG. 7 is a bottom view of a support provided with electrodes.
Figure 8:
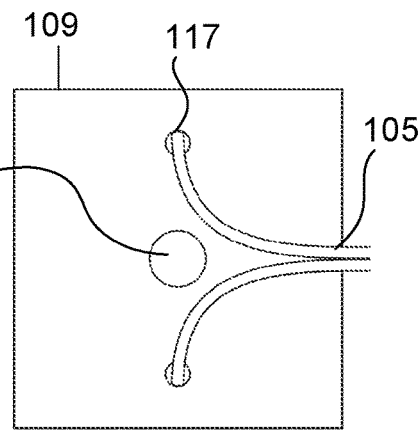
FIG. 8 is a top view of the support of FIG. 7.

The non-conductive support (109) to which the electrodes are attached is shown in FIGS. 7 and 8 and is preferably manufactured from plastics. The support includes access ports (117), shown in FIG. 8, with a radius of 1 mm for providing access for the electric wiring (105) to extend through the support (109). The support further includes an inlet (115) with a radius of 2.2 mm that is located between the electrodes (107) for the delivery of fluid sample to a central region of the square-shaped membrane in use.

The inlet (115) in the support (109) which provides an inlet, communicates with a 17×17 mm recess (121) defined by the support across which the membrane extends in an assembled condition of the device. Delivery through the inlet (115), into the recess (121) defined by the support and onto the membrane may be effected by pipetting the selected volume of fluid sample and injecting it into the inlet (115) using a micropipette. If a micropipette is unavailable, a few drops of fluid sample may be dropped through the inlet onto the membrane. As a rough guideline as to the volume of fluid sample that may be applied dropwise, approximately four drops of liquid equal more or less 200 μl.

Figure 9:
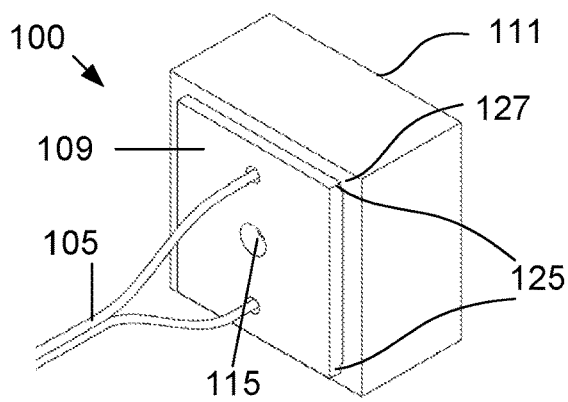
FIG. 9 is a three-dimensional view of a support assembled with a cover.

The support (109) is configured to cooperate with the cover (111) to releasably receive and hold the conductive membrane such that it extends at least partially over the electrodes in order to make contact with the electrodes. The support (109) and cover (111) are shown in FIG. 9 when in an assembled condition with electric wiring (105) extending towards the electrodes attached to the support (109). The support (109) is shaped and sized to be at least partially received within an interior chamber of the cover (111) so that the electrodes attached to the surface of the support (109) are substantially coterminous with an interior surface of the cover (111) opposite the electrodes once the support (109) and cover (111) are assembled. The cover (111) presses against the electrodes (107) when it is assembled with the support (109) thereby holding the membrane captive between the electrodes and the cover (111). The support (109) includes two shoulders (125) extending from opposite sides of the support (109) that, when assembled with the cover (111), extend over a portion of an exterior surface (127) of the cover (111) to limit the extent to which the support is inserted into the cover (111).

The cover (111) ensures that the immediate environment of the membrane is standardized to limit user contact with the membrane during measurements. Ideally the cover of the support must exert the same force on the membrane and the electrodes when it engages with the support. In this embodiment the cover has an 18×18 mm window (135) which allows a user access to the membrane in order to remove or modify it. In an alternative embodiment, the cover may have a closed end.

Figure 10:
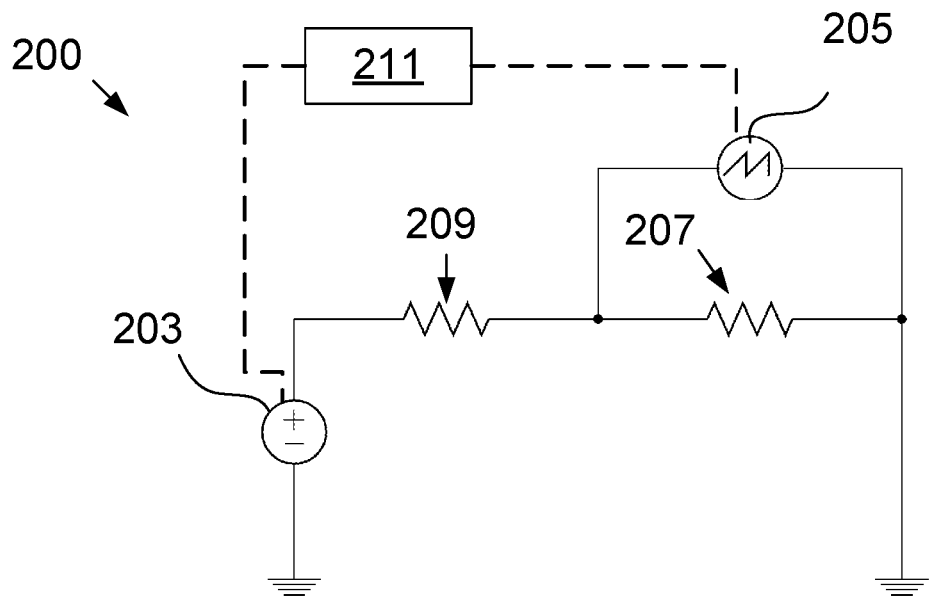
FIG. 10 is a schematic diagram of an electric circuit of an embodiment of the invention.

An embodiment of an electric circuit to which the electric wiring of the device is connected is schematically illustrated in FIG. 10. The electric circuit (200) includes a voltage source (203) which applies a voltage to the electrodes and thus to the membrane (207) which acts as a resistor. Owing to the nature of biological molecules and biological cells, a voltage of between 0.2 V and 0.8 V is applied to avoid damage to the biological recognition component. A second variable resistor (209) is connected in series with the voltage source (203). The resistance of the variable resistor (209) is known and may be adjusted to approximate correlate with the expected resistance across the membrane (207). A resistance monitoring device (205) is provided as part of the circuit and is configured to monitor the resistance of the membrane while a voltage is applied to the membrane by the voltage source (203) as a selected volume of fluid sample onto a central region of the membrane.

The fluid sample is one which is to be tested for the presence of biomolecules capable of binding to the biological recognition components immobilized on the membrane. The fluid sample may be a biological fluid derived from a human or animal, a water sample, or a food sample that has been prepared to provide a suitable fluent sample. The fluid sample may include a buffer solution such as phosphate-buffered saline.

In use, the specific binding of a biomolecule, to a biological recognition component produces a larger molecular complex that is usually not electrically conductive, thus lowering the conductivity of the membrane across the area of binding. Detection of the complexes is possible due to the measurement of an increased resistance and an increased rate of change of the resistance across the membrane. The biomolecule that the membrane is able to detect will depend on the type or the exact biological recognition component immobilized on the membrane.

The device for the detection of biomolecules may be used in a method of detecting biomolecules. Such a method includes at a first step, providing a fluid sample that potentially contains a target biomolecule. Next the fluid sample is delivered onto the membrane of the device described herein, where after the resistance of the membrane is monitored and recorded for a selected period of time. If the resistance increases to above a threshold resistance as determined by a controller, a signal is produced by a signaling component to signify positive detection of a target biomolecule that is known to interact and bind to a selected biological recognition component on the membrane.

An exemplary method for the measurement of primary anti-lysozyme antibodies in sample solutions is described. In this device the biological recognition component is lysozyme which is cross-linked to the conductive membrane.

EXAMPLES

Example 1

The ability of the device to detect the presence of anti-lysozyme antibody was tested with a membrane on which lysozyme is immobilized as the biological recognition component.

Methods

1. Preparation of the Conductive Membrane

A sheet of nonwoven, spun bound and spot melted polypropylene microfibers with a thickness of 50 g/m$^2$ was cut into a 90×90 mm square sheet. The microfibers of the sheet were provided with a conductive coating comprising doped polypyrrole copolymers. The pyrrole monomer was copolymerized with carboxylic acid functional 3-thiopheneacetic acid (3TAA). A 3TAA solution with a concentration of 10 mg/ml was mixed with 10% pyrrole and the microfiber sheet was submerged in the solution for a few seconds and then removed. Thereafter the microfiber sheet was placed in a glass reaction vessel containing 30 ml of 0.1 M iron(III) chloride ($FeCl_3$) in deionised water. A volume of 1 ml of 0.1 M 5-sulfosalicylic acid (5SSA), acting as a dopant, was added for each 10 ml of $FeCl_3$, acting as an oxidant. The reagents were left to react for 30 minutes at room temperature while gently agitated to allow oxidative polymerization of the pyrrole monomer to occur. The microfiber sheet was then removed and washed with deionised water and left to dry for 4 hours.

2. Glutaraldehyde Attachment

The coated conductive microfiber sheets were cut into smaller 30 mm×30 mm membranes. The smaller membranes were washed with distilled water and left to dry for five minutes. The sheets were immersed in 2.5 mM glutaraldehyde solution and incubated at 4° C. for one hour, after which the microfiber membranes were again washed with distilled water and dried for 10 minutes.

3. Lysozyme Immobilization

The conductive glutaraldehyde coated microfiber membranes were washed with distilled water and left to dry for five minutes. A lysozyme solution was made up in sterile glass containers with 100 µg/ml lysozyme derived from chicken egg white protein (Roche, Mannheim, Germany) in phosphate-buffered saline (1×PBS) comprising 137 mmol/L NaCl, 2.7 mmol/L KCl, 10 mmol/L $Na_2HPO_4$ and 1.8 mmol/L $KH_2PO_4$.

The membranes were rinsed with 1×PBS for approximately 10 seconds and then immersed in the lysozyme solution and incubated at 4° C. for 2 hours. Following incubation, the microfiber membranes were washed with 1×PBS and left to dry for 10 minutes.

The amount of biological recognition components, in this case lysozyme, immobilized on the membrane is proportional to the amount of glutaraldehyde present on the microfibers of the membrane. The more biological recognition components on the membrane, the higher the sensitivity of the device due to the potential for more molecular binding of biomolecules. Therefore, it is preferable to immobilise a substantial amount of lysozyme onto the membrane. If, however, the membrane is left in the lysozyme solution for too long, the glutaraldehyde may detach from the membrane due to dissolution. It was found that the rate of lysozyme attachment to the cross-linker usually exceeds the rate of dissolution of glutaraldehyde in the 1×PBS solution.

4. Manufacturing of the Support and Cover

In order to support the membrane and to provide a standardized testing environment for measuring the resistance of the membrane a support that cooperates with a cover was designed using AutoCad™ and the support and cover was fabricated by three-dimensional printing using a MakerBot™ Replicator Z18 3D Printer (2009-2015 MakerBot Industries, LLC One MetroTech Center, 21st Floor, Brooklyn, N.Y. 11201 USA).

5. Preparation of the Fluid Sample: The Antibody Solution

Different concentrations of primary anti-lysozyme antibody solutions were prepared: 313.6, 31.6, 15.8 and 0.8 µg/ml. The antibody solutions were made up by diluting a small quantity of the primary antibody in 10×PBS to the desired concentration.

6. Preparing for Measurements

To ensure that all measurements were standardized, 300 or 500 µl of PBS was delivered onto different membranes so that the membranes are equally saturated with PBS prior to measurements. A membrane was then placed on the support and covered with the cover. Resistance measurements were carried out by connecting the membrane prepared by the methods described above to the electric circuit shown in FIG. 10 by means of the electrodes attached to the support. An oscilloscope (Tektronix TDS 1002b) was used to measure the potential difference across the membrane. The oscilloscope was connected to a computer which processed the results.

A constant 0.5 V was selected and the voltage source was set to this value. The measured voltage at each time point could be used in calculating the resistance of the membrane by Ohm's law, R=V/I, wherein, R is the resistance, V is the potential difference (or voltage) across the membrane and I is the current in the circuit. The resistance of the membrane was calculated from the difference between the applied voltage and the voltage measured in the circuit. Using Kirchoff's rule the following equation was determined for the experimental setup described above:

$$-V_i + V_R + V_f = 0$$

where $V_i$ is the source voltage, $V_R$ is the voltage across the variable resistor and $V_f$ is the difference between the applied voltage and the voltage measured (the voltage drop) over the membrane. The above equation can be expanded to:

$$V_i = R_s \times i + V_f$$

$V_f$ was measured continuously by the oscilloscope. With the only unknown variable being i, the current, and using Ohm's law (R=V/I), the two equations can be combined to calculate the resistance at any given time:

$$R_f = \frac{V_f R_s}{-V_f + V_i}$$

With an expected resistance of a membrane in the range of 1000Ω, the resistance of the variable resistor ($R_s$) was selected to be 1000Ω. With the oscilloscope measuring the voltage drop over the membrane, the resistance of the membrane can be calculated using the following equation:

$$R_f = \frac{V_f \times 1000}{-V_f + 0.5}$$

Using Matlab™ and Control System Toolbox® the resistance measurements (voltage drops) were recorded and analyzed.

After about 10 seconds of applying a voltage to the membrane, 200 µl of antibody solution at a chosen concentration was added through the opening in the support to deliver the solution onto the membrane. The primary anti-lysozyme antibodies bind to the lysosome to form an antigen-antibody complex, which was found to exist for up to an hour. Thus after the antibody was added, the resistance was measured and recorded for an hour.

7. Data Capturing

Four different sets of data from the following experiments were captured:
(a) Resistance of the membrane with the conductive coating;
(b) Resistance of conductive membranes with glutaraldehyde attached to it;
(c) Resistance of conductive membranes with both glutaraldehyde and lysozyme attached; and
(d) Resistance of conductive membranes with glutaraldehyde, lysozyme and different concentrations of antibody attached;

Each of these experiments were run on a set of three to four different membranes prepared by the same process to assess the repeatability of the results and the accuracy thereof. The data from each test was interpreted and a graph displaying the resistance over time plotted.

In the plots shown in the results section below, the measurements between the experimental start time, which is the moment that a solution is delivered to the membrane across which a voltage is applied, and one minute are not shown. It was found that the addition of the solution during this time period resulted in anomalous and erratic resistance measurements which were non-linear. The anomalous readings are to be expected, as it is difficult to control the rate of the delivery of the solutions onto the membrane.

8. Qualitative Tests Conducted to Confirm Binding of Anti-Lysozyme Antibodies to Lysozyme Immobilized on a Membrane Positive binding of the antibodies to the protein and thus to the membrane was confirmed by staining the microfibers of the membrane with a secondary fluorescent antibody in a separate experiment. Following the immobilization of lysozyme onto the membrane, the membrane was placed in a container containing 200 µl of 313.6 µg/ml anti-lysozyme antibody solution and incubated at 4° C. for an hour. The membrane was then thoroughly washed with 1×PBS to remove any excess anti-lysozyme antibodies that did not bind to the lysozyme. The following steps were then carried out in a dark room due to the light sensitivity of the fluorochromes in the reagents. 200 µl of the secondary antibody, Alexa Fluor 488 (Invitrogen), was delivered onto the membrane and the membrane was incubated at room temperature for an hour before again being washed with 1×PBS and left to dry. Treated samples were then stored in a light sensitive container. Confirmation of positive binding of the protein to the fiber and the primary antibody to the protein was established using a fluorescent confocal microscope (Zeiss LSM780 confocal microscope). Positive and control images were captured with the 40× objective and the fluorescence and phase contrast overlays were qualitatively assessed. The fluorescent secondary antibodies immobilized on microfibers of the membrane are clearly visible on the images taken.

Experimental Results (a) Resistance of the Membrane with the Conductive Coating

In the first experiment, the resistance, calculated from the voltage drop across three membranes coated with the conductive coating, were measured over 20 minutes. The three membranes were prepared by the same process described above at 1. The resistance as a function of time of the three membrane are plotted in FIG. 11. Linear trend lines were fitted to each set of data (membrane 1 (1001): y=3.7511x+ 238.98R²=0.9231, membrane 2 (1002): y=2.4567x+

135.48$R^2$=0.9712, membrane 3 (1003): y=2.5994x+217.12$R^2$=0.9336)). An increase in resistance, or decrease in conductivity, over time is observed for each membrane. The initial resistance and the rate of increase in resistance in the plots are more or less similar for the different membranes.

Following the coating the sheets with conductive reagents, membrane resistance values of as low as 140Ω per 17 mm were achieved. 17 mm is the standardized distance over which measurements were taken. Although low resistances were achieved, the resistance of the three membranes prepared varied between 140Ω and 300Ω over the 17 mm distance. It is foreseen that this variance may be reduced by automatization of the membrane preparation process.

Figure 11:
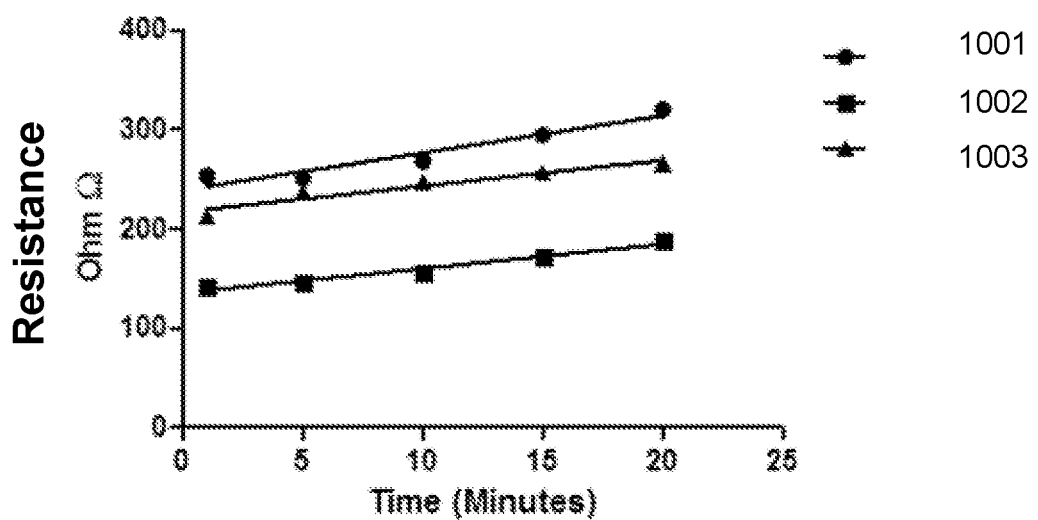
FIG. 11 is a graph showing the resistance of three different conductive membranes, prepared by the same process, as a function of time.

The steady increase in resistance over time, shown in FIG. 11, occurs even though no additional solutions or reagents were applied to the membrane during measurements. The applicant believes the increase in the resistance is caused by interactions of the copper electrodes, and the salts present on the membrane such as the iron(III)chloride, sodium chloride (NaCl), potassium chloride (KCl), sodium phosphate ($Na_2HPO_4$) and potassium phosphate ($KH_2PO_4$) derived from the PBS solution which was applied to the membrane before all measurements.

The linear increase in the resistance observed, are expected to be present in all resistive measurements to be carried out on the membranes. It may be described as a "base response" or background response to which all further measurements may be compared. The rate of increase in the resistance was averaged based on the data in FIG. 11 to be approximately 2.935Ω per minute.

Figure 12:
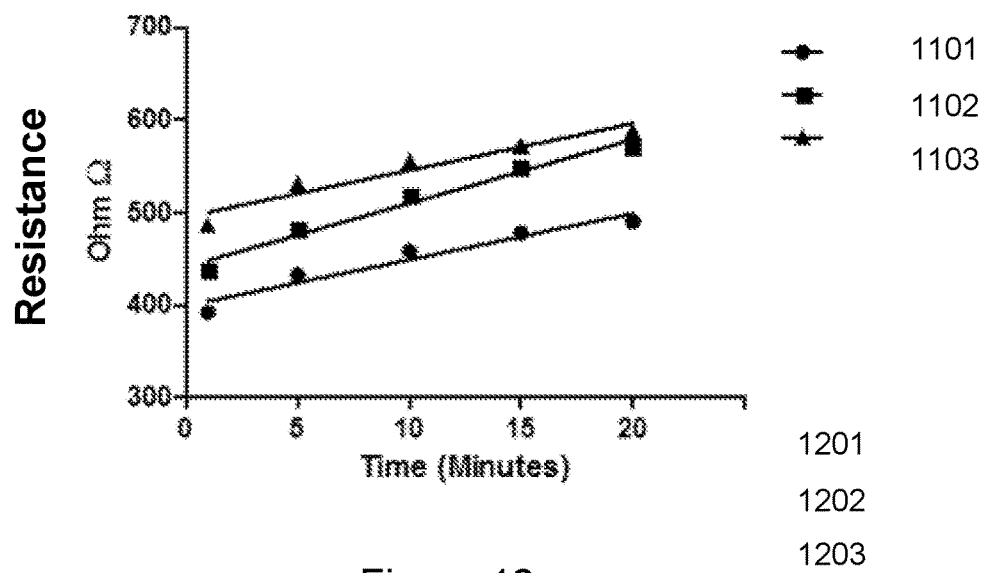
FIG. 12 is a graph showing the resistance of three different conductive membranes to which the cross-linking reagent glutaraldehyde has been attached as a function of time.

(b) Resistance of Conductive Membranes with Glutaraldehyde Attached to it;

In the second experiment, the resistance, calculated from the voltage drop across three conductive membranes to which the cross-linking reagent glutaraldehyde has been attached was measured over 20 minutes and a plot of the results is shown in FIG. 12. Linear trend lines were fitted to the plots (membrane 1 (1101): y=4.9836x+399.43$R^2$=0.9355, membrane 2 (1102): y=6.8606x+441.49$R^2$=0.9752, membrane 3 (1103): y=5.0314x+495.38$R^2$=0.9231). The initial resistance of the three membranes are different, however, the rate of increase of the resistance over time are very similar.

The layering of the membrane with glutaraldehyde decreased the conductivity of the membrane. The resistance of a conductive membrane after glutaraldehyde attachment increased with between 200Ω and 350Ω. An average of the measured resistance for the three membranes produces a trend line, y=5.6252x+445.43, with the gradient displaying the increase in resistance per minute. The rate of increase of the resistance is higher in comparison to the rates of increase observed for the membranes without glutaraldehyde, probably due to the fact that conducting pathways have been covered with the glutaraldehyde cross linker.

Further experiments showed that longer incubation times and higher concentrations of glutaraldehyde increased the resistance of the membrane further due to multi-layering. Thus it was found that the optimal incubation time and concentration of glutaraldehyde at which maximum glutaraldehyde is attached without creating multilayers is between 1 and 2 hours, preferably 1.5 hours and a concentration of 2.5 v mM glutaraldehyde.

Figure 13:
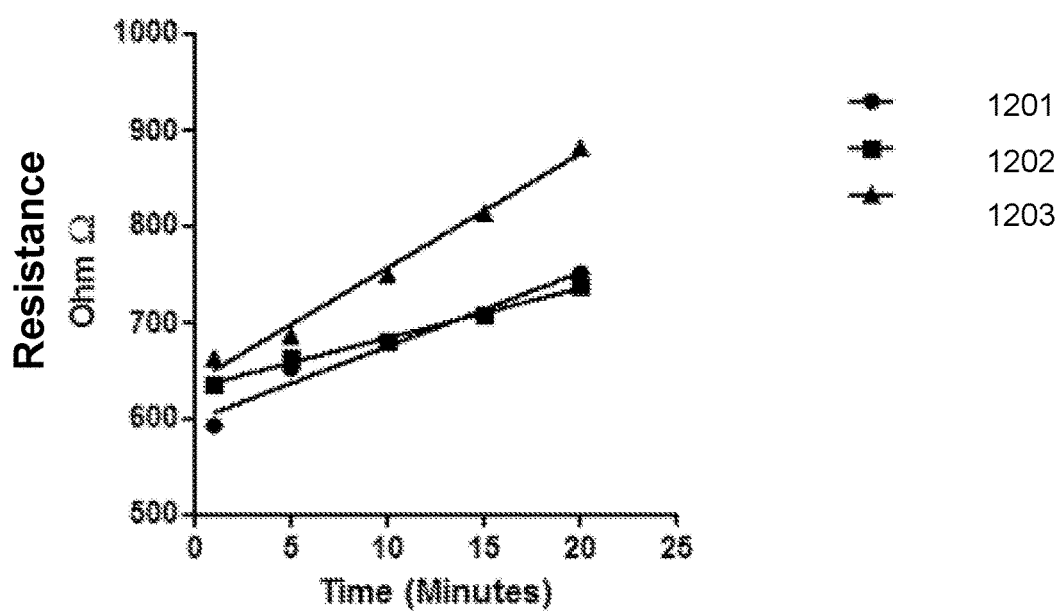
FIG. 13 is a graph showing the resistance of three different conductive membranes to which a cross-linking reagent, glutaraldehyde, and lysozyme protein have been attached, as a function of time.

(c) Resistance of Conductive Membranes with Both Glutaraldehyde and Lysozyme Attached Thirdly, the resistance, calculated from the voltage drop across three conductive membranes to which the cross-linking reagent glutaraldehyde and the lysozyme protein have been attached were measured over 20 minutes and a plot of the results is shown in FIG. 13. Linear trend lines were fitted to the plots (membrane 1 (1201): y=7.6702x+598.54$R^2$=0.9661, membrane 2 (1202): y=5.1633x+632.5$R^2$=0.9903, membrane 3 (1203): y=11.826x+638.53$R^2$=0.9889).

The immobilization of lysozyme on the membrane further increased the resistance of the membrane by between 100Ω and 300Ω. An average of the measured resistance for the three membranes produces a trend line with equation: y=8.2199x+623.19.

Figure 14:
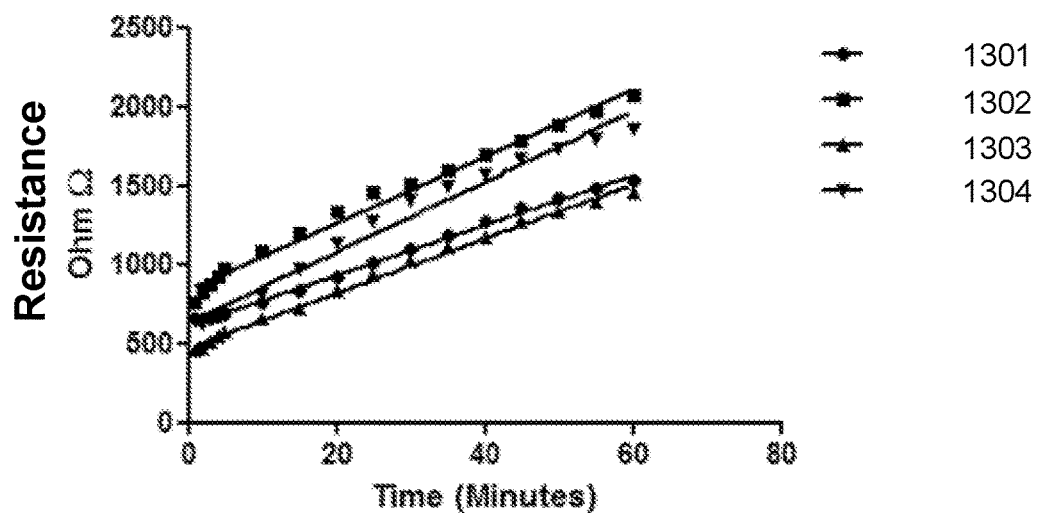
FIG. 14 is a graph showing the resistance as a function of time of four different conductive membranes with lysozyme onto which 200 µl of 313.6 µl/ml antibody solution was applied.

(d) Resistance of Conductive Membranes with Glutaraldehyde, Lysozyme and 200 µl of Different Concentrations of Antibody Added onto the Membranes Resistance measurements were taken every 2 seconds for the first 5 minutes of the experiments, and thereafter a reading was taken every minute for one hour. A plot of the resistance of four different membranes prepared by the same process and onto which 200 µl of 313.6 µl/ml (100× diluted antibody) antibody has been applied is shown in FIG. 14. The linear trend lines fitted to the four graphs are summarized in Table 1:

TABLE 1

Linear trend lines of the plots in FIG. 14

| Membrane | Label in FIG. | Trend line equation |
| --- | --- | --- |
| 1 | (1301) | y = 15.887x + 613.97, $R^2$ = 0.9971 |
| 2 | (1302) | y = 21.273x + 837.13, $R^2$ = 0.9878 |
| 3 | (1303) | y = 17.259x + 472.15, $R^2$ = 0.9955 |
| 4 | (1304) | y = 22.358x + 631.32, $R^2$ = 0.9803 |

FIG. 14 shows a considerable increase in the resistance of each membrane in the first 5 minutes after the antibody solution was added to the membrane. After 5 minutes the rate of change of the resistance decreases. The initial resistance measured for each membrane differs by approximately 200Ω. The rate of increase of the resistance over 60 minutes varies between approximately 16 and 22Ω per minute.

Figure 15:
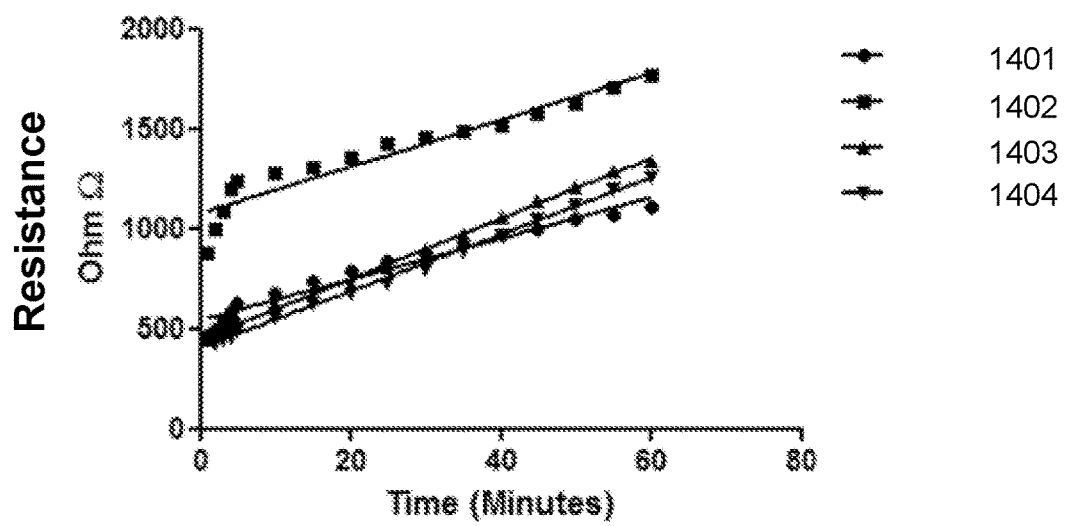
FIG. 15 is a graph showing four plots of the resistance as a function of time of four different conductive membranes with lysozyme onto which 200 µl of 15.8 µl/ml antibody solution was applied.

A plot of the resistance of four different membranes prepared by the same process and onto which 200 µl of 15.8 µl/ml (10 000× diluted antibody) is shown in FIG. 15. The linear trend lines fitted to the last 55 minutes (thus excluding the first 5 minutes that show a rapid increase in resistance) of the four graphs are summarized in Table 2:

TABLE 2

Linear trend lines of the plots in FIG. 15

| Membrane | Label in FIG. | Trend line equation |
| --- | --- | --- |
| 1 | (1401) | y = 10.179x + 542.12, $R^2$ = 0.9628, |
| 2 | (1402) | y = 11.719x + 1074.9, $R^2$ = 0.902 |
| 3 | (1403) | y = 15.066x + 447.11, $R^2$ = 0.9976 |
| 4 | (1405) | y = 14.134x + 405.47, $R^2$ = 0.9974 |

As can be seen in FIG. 15, even at this considerably lower concentration of antibody solution of 15.8 µl/ml, there is an immediate, measurable increase in the resistance of the membrane after the antibody solution has been delivered onto the membrane. The rate of the increase in the resistance after 5 minutes are similar for the four different membranes.

Figure 16:
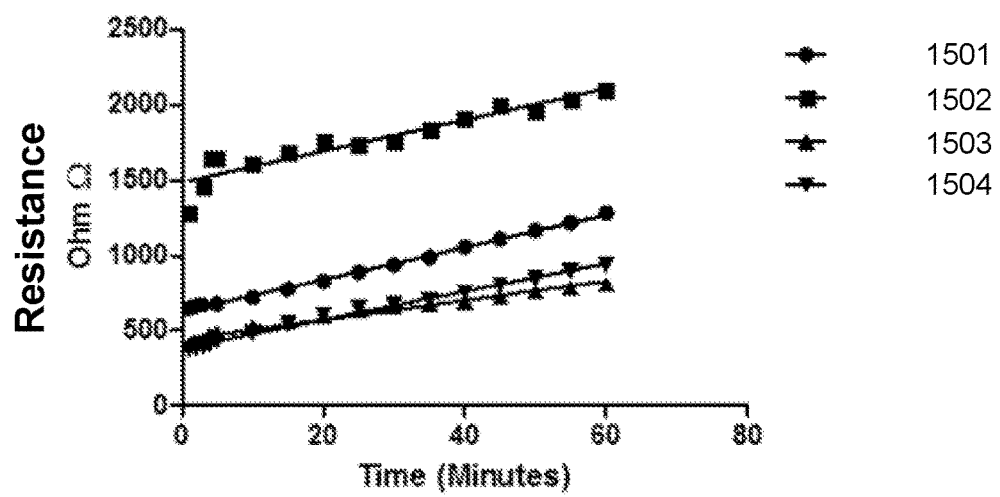
FIG. 16 is a graph showing four plots of the resistance as a function of time of four different conductive membranes with lysozyme onto which 200 µl of 0.8 µl/ml antibody solution was applied.

Next, a plot of the resistance of four different membranes prepared by the same process and onto which 200 µl of 0.8 µl/ml (100 000× diluted antibody) is shown in FIG. 16. The linear trend lines fitted to the four graphs are summarized in Table 3:

TABLE 3

Linear trend lines of the plots in FIG. 16

| Membrane | Label in FIG. | Trend line equation |
|---|---|---|
| 1 | (1501) | y = 10.767x + 622.87, $R^2$ = 0.9976 |
| 2 | (1502) | y = 10.32x + 1486, $R^2$ = 0.8745 |
| 3 | (1503) | y = 6.4755x + 438.37, $R^2$ = 0.9702 |
| 4 | (1504) | y = 9.4595x + 379.73, $R^2$ = 0.9922 |

As is evident from FIG. 16, even at the extremely low antibody solution concentration of 0.8 μl/ml, an rapid increase of the resistance of the membrane in the first 5 minutes of the experiment is observed. Thereafter, more or less the same rate of increase of the resistance is observed in the four different membranes.

Figure 17:
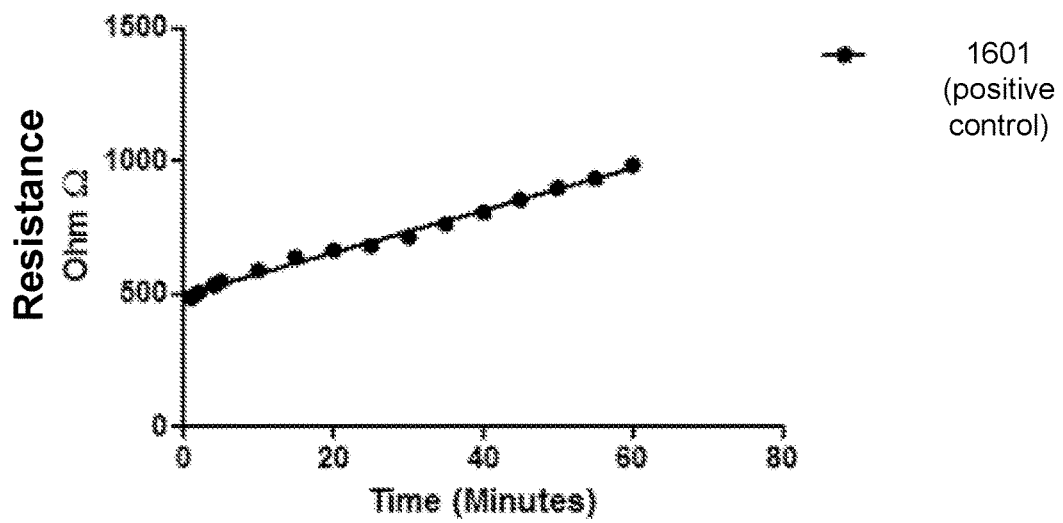
FIG. 17 is a graph of the resistance as a function of time of a conductive membrane with lysozyme to 200 µl of a 15.8 µl/ml antibody solution containing an antibody non-specific to lysozyme was applied.

To verify the results, a positive control test was performed. 200 μl of a 15.8 μl/ml antibody solution containing an antibody non-specific to lysozyme was applied to the conductive membrane on which lysozyme was immobilized and the resistance of the membrane was measured over the course of an hour. The results of the positive control test is shown in FIG. 17. The linear trend line (1601) fitted to the plot is of the form y=7.9448x+495.41, $R^2$=0.9939. The gradient of the linear trend line is similar to that of the conductive membrane to which glutaraldehyde and lysozyme has been attached. The plot therefore confirms that the addition of non-specific antibodies to the membrane does not result in a rapid increase in resistivity of the membrane, as was observed with the specific binding of anti-lysozyme antibodies to the lysozyme immobilized on the membrane.

The results obtained for the experiments involving the delivery of the three different concentrations of anti-lysozyme antibody onto four different membranes prepared by the same process were combined. The combined plots for each concentration and the results of the positive control test, as well as the results of a negative control test, during which only PBS solution containing no biomolecules is delivered onto the membrane, are shown in FIG. 18.

The linear trend lines for the respective concentrations and the control tests are listed in Table 4:

TABLE 4

Figure 18:
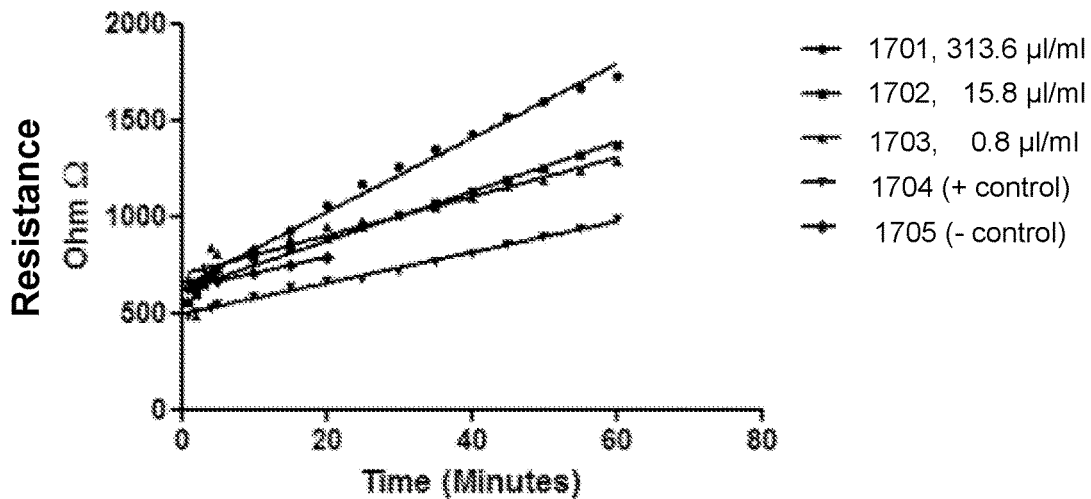
FIG. 18 is a graph showing combined plots of the resistance of the membrane as a function of time for each of the different concentrations of antibody solution applied to the membrane (313.6, 15.8 and 0.8 µl/ml); further including a combined plot for the application of a non-specific antibody and a solution containing no antibodies as a positive and negative control respectively.

Linear trend lines of the plots in FIG. 18

| Concentration of anti-lysozyme antibody solution (μl/ml) | Concentration of non-specific antibody solution (μl/ml) | Label in FIG. | Trend line equation |
|---|---|---|---|
| 313.6 | — | (1701) | y = 19.203x + 638.25, $R^2$ = 0.9941 |
| 15.8 | — | (1702) | y = 12.775x + 617.39, $R^2$ = 0.9875 |
| 0.8 | — | (1703) | y = 10.046x + 698.71, $R^2$ = 0.8946 |
| — | 15.8 | (1704) | y = 7.9448x + 495.41, $R^2$ = 0.9939 |
| 0 | — | (1705) | y = 8.2199x + 623.19, $R^2$ = 0.9978 |

As is evident in FIG. 18, a pronounced initial response in the form of a substantial increase in the resistance of the membrane in the first few minutes after application of the anti-lysozyme antibodies to the membrane is observed with all of the different concentrations of the antibody solution. In these cases, the rate of increase of the resistance decreases but remains constant after the first 5 minutes over the course of the next 55 minutes. It is clear from FIG. 18 that there is substantially no such response in the positive (non-specific antibody solution) and negative control tests (zero concentrations of antibody solution).

The gradients of the linear trend lines of FIG. 18, indicate the rate of increase in the resistance of the membrane is highest when the 313.6 μl/ml concentration of anti-lysozyme antibodies is applied to the membrane. The rate of increase of resistance of the membrane when anti-lysozyme antibodies at a concentration of 15.8 μl/ml and 0.8 μl/ml is applied to the membrane is lower than that of the 313.6 μl/ml concentration. The gradient of the measured resistance at the concentration of 0.8 μl/ml is very similar to that of the concentration of 15.8 μl/ml which is indicative of the sensitivity of the device.

The rate of increase of resistance of the membrane when it is treated with a non-specific antibody (positive control) or without any type of antibody (negative control) are similar at approximately 8Ω per minute.

Figure 19:
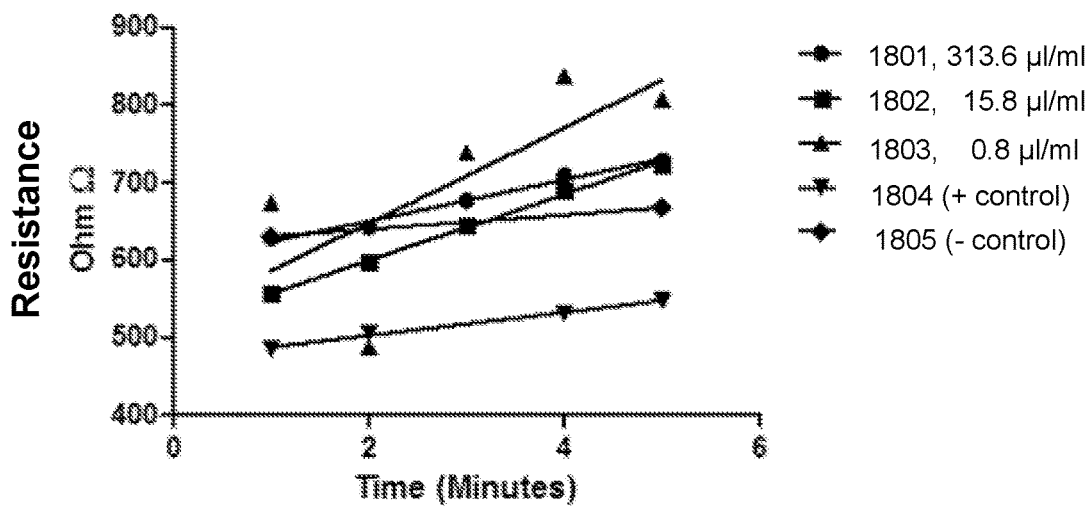
FIG. 19 is a graph showing the first five minutes of the combined plots of the resistance as a function of time of FIG. 18.

FIG. 19 is a plot of the first 5 minutes of the results shown in FIG. 18. The linear trend line equations and the rate of the increase in the resistance of the membrane during the first 5 minutes after addition of the solution to the membrane to which a voltage is applied is summarized in Table 5.

TABLE 5

The linear trend lines of the plots in FIG. 19 and the rate of change of the resistance

| Concentration of anti-lysozyme antibody solution (μl/ml) | Concentration of non-specific antibody solution (μl/ml) | Label in FIG. | Trend line equation | Rate of change of the resistance (Ω/min) |
|---|---|---|---|---|
| 313.6 | — | (1801) | y = 26.821x + 596.64, $R^2$ = 0.9818 | 26.8 |
| 15.8 | — | (1802) | y = 42.852x + 513.48, $R^2$ = 0.9973 | 42.9 |
| 0.8 | — | (1803) | y = 61.584x + 524.0, $R^2$ = 0.4905 | 61.6 |
| — | 15.8 | (1804) | y = 14.992x + 472.46, $R^2$ = 0.9935 | 15.0 |
| 0 | — | (1805) | y = 9.4016x + 620.93, $R^2$ = 1 | 9.4 |

The rate of increase of the resistance of the membrane over the period of 5 minutes from the application of the anti-lysozyme antibody solution to the membrane is much higher than the rate of increase of the resistance of the membrane to which a zero concentration of antibody (negative control) or a non-specific antibody solution (positive control) was applied.

The results show that the antibodies in the solution can be detected using an embodiment of the device for the detection of biomolecules. The fact that a measurable resistance response was obtained at an antibody concentration of 0.8 μl/ml in comparison to the negative control shows that the membrane is remarkably sensitive to very low concentrations of antibody.

The positive control serves to show that the increase in the rate of change of the resistance is as a result of specific binding occurring between the anti-lysozyme antibody and the lysozyme, and not due to non-specific antibody binding or adsorption of the antibody to the membrane.

The application of the antibody to the membrane resulted in the antibody binding to the lysozyme to form an antigen-antibody complex. During the first few minutes of monitoring the resistance following application of the antibody solution, a marked increase in resistance, at an increased rate relative to the remainder of the time that the resistance was monitored, was observed. The positive and negative control tests conducted had a rate of increase in resistance of 14.992Ω per minute and 9.4016Ω per minute respectively for the first five minutes. The experiments conducted with varying concentrations of antibody showed an average increase in resistance of 26.821, 42.852 and 61.584Ω per minute over the first five minutes respectively. These results suggest that binding between the antibody and lysozyme occurs from immediately after the antibody has been added at a relatively rapid rate.

The results also indicate that the device appears to be most effective to detect the presence of the antibody within the first five minutes or less of adding the sample, rather than running the experiment for a full hour. The rate of increase in resistance was slightly less discerning, although still reasonably higher in comparison to the control measurements for the remainder of the time period from 6 to 60 minutes. By extending the duration of the measurements, one may be able to more accurately determine the approximate concentration of antibodies in the sample solution.

It is expected that the larger the antigen-antibody complex (or the biological recognition component and biomolecule combination) bound to the membrane following addition of the sample solution to the membrane, the higher the resistance of the membrane and the more pronounced the difference between the resistance of the membrane with the complex and the resistance of the membrane without the complex.

In the experiments carried out the sheets of the nonwoven, spun bound spot melted polypropylene microfibers had a thickness or areal density of 50 g/m² which provided a sufficiently large surface area for the immobilization of the biological recognition component onto the membrane. The sheets also had the desired durability. It is foreseen that sheets of various thicknesses or areal densities may be used in the preparation of a membrane, however, the use of a thicker material allowed the solution delivered onto the membrane during use to permeate through the microfibers more slowly, allowing more time for specific binding of the biomolecules to the biological recognition component. If thinner sheets were used the solution may simply flow through the cavities in the membrane without allowing time for binding to occur.

Example 2

The ability of the device to detect *Escherichia coli* (*E. coli*) bacteria was tested. The conductive membrane was prepared according to the steps in Example 1 above. However, instead of lysozyme, Anti-*E. coli* antibody ab25823 was immobilized on the membrane.

Methods

The immobilization of Anti-*E. coli* antibody ab25823 onto the membrane was achieved by firstly washing the conductive membrane with 0.01M PBS and drying it for 10 minutes. The membrane was then incubated in 2.5 mM glutaraldehyde for 1 hour at 4° C. Thereafter, the membrane was washed again with 0.01M PBS and dried for 10 minutes. The membrane was incubated in 600 mL Anti-*E. coli* antibody (6.67 ug/mL) at 37° C. for 1 hour and thereafter washed with 0.01M PBS and dried for 10 minutes. Thereafter 5% BSA Blocker™ was added to the membrane and it was left to react for 1 hour at room temperature. Finally the membrane was washed three times using 0.01M PBS.

Different concentrations of *E. coli* solutions of $3.4 \times 10^8$, $3.4 \times 10^5$ en $3.4 \times 10^2$ CFU/ml were prepared and 100 μl of each solution was delivered onto a membrane. The experiments were repeated using three similarly prepared conductive membranes with anti-*E. coli* antibody immobilized thereon. Further control experiments were conducted in which 100 μl of $9.67 \times 10^7$, $9.67 \times 10^4$ en $9.67 \times 10$ CFU/ml solutions of *Lacto Bacillus Plantarum* bacteria were delivered onto the membranes having anti-*E. coli* antibody immobilized thereon.

Results

Figure 20:
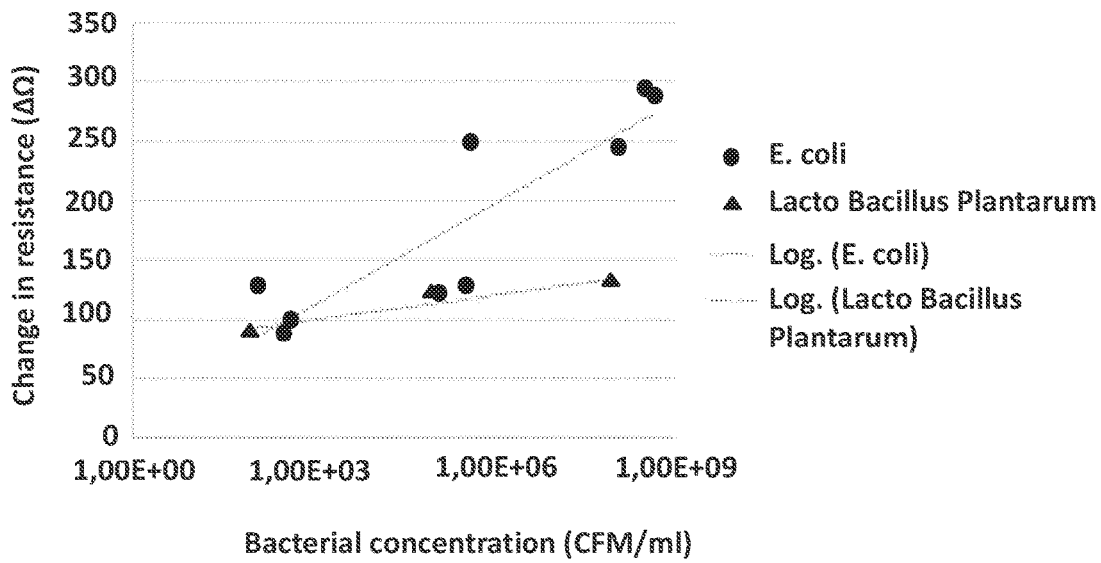
FIG. 20 is a graph showing the increase in the resistance of the membrane after the first five minutes as a function of bacterial concentration.

The results of the experiments are shown in FIG. 20 which is a plot of the change in the resistance of the membranes in the first five minutes of each experiment following addition of the bacterial solutions. The graph shows that at the highest concentration of *E. coli* there is a marked increase in the rate of change of the resistance of the membrane when the *E. coli* solution is added to the membrane. In contrast, no substantial increase can be noted when *Lacto Bacillus Plantarum* is delivered on the membrane. Accordingly, the specific binding of *E. coli* to the anti-*E. coli* antibody immobilized on the membrane results in a marked increase in the rate of change of the resistance of the membrane allowing for the detection of *E. coli*.

*E. coli* binding was also confirmed by staining live bacteria cells and observing the stained bacteria under a confocal microscope.

Example 3

In this example a paper-based conductive membrane was used as part of the device to demonstrate its ability to detect anti-lysozyme antibodies. Lysozyme protein was immobilized on the paper-based conductive membrane and the resistance of the membrane was monitored and recorded. The resistance measurements were processed and demonstrate that the paper-based conductive membrane is capable of resistive sensing of biomolecules.

Methods

Whatmann Grade 50 (97 g/m$^2$) and Whatmann Grade 1 (87 g/m$^2$) Filter Papers were chosen and acquired from Sigma Aldrich due to their wet strength. Whatmann Filter Papers (Grades 1,50) were cut into a standard size of 180×280 mm to be used for testing.

1. Conductive Coating

The cellulose fibers of the filter paper were made conductive through coating with a doped polypyrrole solution. The 180×280 mm sheets were first immersed in the pyrrole monomer and left to soak for 5 minutes, this ensured that the paper was fully saturated with the pyrrole. The pyrrole saturated sheets were then immersed in a solution containing 0.3M HCl and 5 g/100 ml FeCl$_3$ in distilled water and left to polymerize for 90 minutes. The paper sheets were gently agitated to allow oxidative polymerization to occur. The fibers were removed from the reaction vessel and washed with 0.3M HCl and deionized (DI) water to remove excess pyrrole. The paper sheets were then placed in a fume-hood and left to dry for 1 hour. The treated paper sheets exhibited surface depositions of excess pyrrole and iron, therefore the conductive sheets were further cleaned through mechanical means. The mechanically cleaned sheets were then washed with DI water and left to dry in the fume-hood. Paper coated with this method to form a conductive membrane displayed high electrical conductivity (15 S cm$^{-1}$) and good mechanical stability. The conductive papers (180×280 mm) displayed resistances in the 2-5Ω range measured across the width of the sheet and not its length.

2. Glutaraldehyde Cross Linking

The membranes were immersed in a solution of DI water containing 2.5 mM glutaraldehyde. Incubation was allowed to continue at 4° C. for an hour, after which the membranes were removed, washed with DI water and left to dry. The resistance of the membranes increased by 1-3Ω after glutaraldehyde was linked to the membrane.

3. Lysozyme Attachment

Lysozyme protein, from chicken egg whites (Roche, Mannheim, Germany), was made up in a solution with 1 mg/ml concentration in 1×PBS, this solution was prepared in the sterilized glassware. The glutaraldehyde PPy-paper sheets were rinsed with 1×PBS for approximately 5 seconds and transferred into the lysozyme solution container. The sheets were left to incubate in the lysozyme solution at 4° C. for 2 hours. Post incubation the labeled paper sheets were washed with 1×PBS and left to dry.

4. Experimental Setup

Resistive sensing was implemented through the use of an Arduino Uno microprocessor and dedicated circuitry. The dedicated circuitry is shown in FIG. 10 and functions as an ohmmeter where the unknown resistance, the conductive membrane with lysozyme immobilized thereon, is measured through voltage division by measuring the voltage drop across a known resistor. The experimental method allowed for use of the Arduino microprocessor to pass information through it's analog pin (A0), to a laptop's serial monitor. The input voltage was 0.5 V.

Once the membranes with lysozyme immobilized thereon have dried, each membrane was placed onto the electrodes and a base resistance for that individual membrane was measured and recorded over 1 minute. The configuration of the electrodes were chosen such that membrane was sandwiched between the copper plates acting as the electrodes. This electrode configuration measures resistance through the electrotextile's width.

5. Preparation of Antibody Solutions to be Tested

Concentrations of anti-Lysozyme antibodies were made up in 1×PBS: 1110.14, 111.01, 11.01, 1.10, 0.11, 0.01 μg/ml. The range of dilutions allowed for a limit-of-detection (LOD) to be identified.

A volume of 100 μl of anti-Lysozyme antibody was then added to the fibers and they were left to incubate at 4° C. for an hour. This ensured that as many of the available binding sites on the paper were utilized. Post-incubation, the paper sheets were rinsed with 1×PBS briefly, to ensure that no non-bound anti-lysozyme antibodies, or other biological matter remained on the surface and affected the resistance readings. After the fibers were washed, they were allowed to air dry. The dry paper sheets, immobilized with antibodies, were then placed on the support and individual resistance measurements were recorded for 10 minutes. Measurements taken within the first minute were ignored.

Tests were repeated on at least 3 and up to 7 papers for each concentration of antibodies in order to prove repeatability and to provide a larger data set. Ratios of resistances measured after incubation to baseline resistances were constructed in order to try discern if there is a rational resistance increase for each concentration of antibodies.

Results

Lysozyme and primary antibodies were characterized using a secondary fluorescent antibody (Alexa Fluor 488) and fluorescent images were taken using a Zeiss™ LSM780 (confocal microscope). Primary anti-lysozyme antibodies were added to the membranes immobilized with lysozyme. Alexa Fluor 488 was added to the papers treated with primary antibodies, membranes with only lysozyme immobilized and membranes lacking glutaraldehyde.

Binding of the secondary fluorescent antibody to the primary anti-Lysozyme antibodies was confirmed through confocal microscopy. Fluorescence in the image indicates presence of the secondary, primary antibodies and thus lysozyme protein. Uniform coating of the individual fibers was observed, singular fibers could be made out due to fluorescent antibodies binding around the fibers. Control tests were performed on the membranes and papers untreated with primary antibody, specific binding was confirmed due to the lack of fluorescence in the control images.

Figure 21:
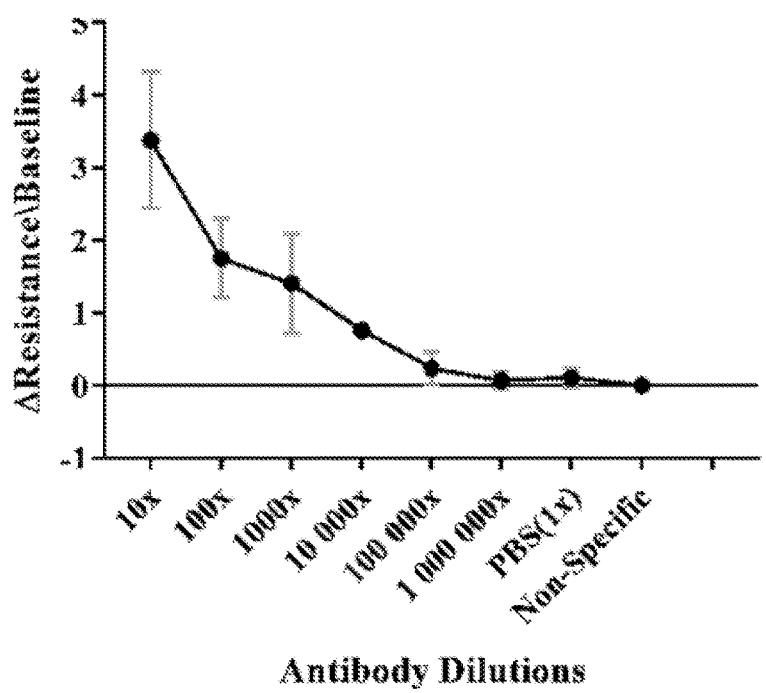
FIG. 21 is a plot of the change in the resistance of paper-based membranes from a baseline resistance following the addition of an anti-lysozyme antibody solution to the paper-based membrane having lysozyme immobilized thereon.

From the resistance measurements, a rational resistance increase was calculated for each membrane and these calculated values were compared to antibody concentrations, positive and negative controls. The results are shown in FIG. 21. The highest concentration antibody solution displayed the greatest rational resistance increase. It was noted that resistance increased dramatically for higher concentrations of antibodies and exponentially declined for each respective dilution thereafter. A positive (non-specific antibody) and negative control (1×PBS) were included in order to discern where the concentration of antibodies produced no noted increase over the controls. A limit-of-detection (LOD) of 100 ng/ml was calculated.

This electrode configuration in this example measured the resistance through the membrane's thickness. Indicating that the size of the membrane can be substantially reduced allowing for miniaturization of the entire device. Such sensing papers could be integrated into micro-controllers, providing on-chip analysis of pathogens.

The results demonstrate that a target pathogen's specific antibody could be immobilized to the cellulose fibers' surface and the same methodology of testing could be applied, resulting in a resistance increase across the membrane. Pathogens may be substantially larger in size than the proof-of-concept protein (lysozyme) used and thus could potentially induce a larger increase in resistance than measured during lysozyme testing.

The device described herein aims to provide a cost effective, efficient and portable impedance based biosensor for rapidly detecting pathogens or antibodies linked to pathogenic infections from a microfluidic sample. Pathogens such as *E. coli* or *Mycobacterium tuberculosis* may be detected, for example. The device may be operated without extra equipment or in depth technical knowledge. The small scale on which the samples are analyzed provides benefits such as smaller amounts of reagents and samples needed, as well as quick throughput screening of the samples.

In essence the device consists of a transducer and biological recognition components that are able to detect the presence and amount of biomolecules present in a sample. The transducer converts the biological response experienced when the biological recognition component interacts with the biomolecules in a sample into an electrical signal that can be quantified.

The device for detecting target biomolecules described herein, is a smaller and lighter alternative to current devices available and is robust, fast acting and highly sensitive to a target biomolecule. The described detection method may also be an inexpensive alternative to current methods available and therefore particularly relevant to contributing to alleviating the diagnostic burden faced with particular pathogens like those of tuberculosis and *E. coli*. The device aims to provide highly specific, rapid detection of the target biomolecule such as an antigen or antibody.

The fact that the membrane and electrodes are not submerged in a buffer solution results in increased sensitivity of the membrane and there is no parallel resistance of the solution to be accounted for.

It will be appreciated that numerous changes may be made to the device for detecting target biomolecules without departing from the scope of the invention. The membrane and the support may be of any suitable size and shape and scaled in accordance with the volume of sample to be delivered onto the membrane. The membrane may be made of any suitable micro or nanofiber that provides a large surface area for the immobilization of biological recognition elements on its surface and which can be modified to be conductive. The membrane may have any suitable thickness or areal density, and the thickness can for instance range between 5 and 100 $g/m^2$.

It will be appreciated that more than one type of biological recognition component may be immobilized on the surface to allow for dual testing for different pathogens, contaminants or infections.

Any type of micro or nanofibers, in the form of a textile may be used as the membrane, provided it is inherently conductive or may be modified to be conductive. The membrane can be made conductive with the appropriate reagents to act as resistor that provides a large surface area for the binding of biological recognition components and potential binding of biomolecules. Depending on the materials used to form the membrane, it may have different surface properties. For example, the membrane prepared from polypropylene microfibers coated with doped polypyrole described in example 1 and 2 above results in a hydrophobic surface. A membrane prepared from cellulosic fibers, as described in example 3, is more hydrophilic resulting in a different interaction of an aqueous sample containing biomolecules with the membrane. It has been found that paper used as a substrate in the conductive membrane is more absorptive thereby affecting the dispersion of the fluid sample containing biomolecules across the membrane. The use of paper as the membrane is advantageous due to its wide availability and affordability. The cellulose fibers have a high surface area and a wide range of fiber diameters can be found in paper.

The support may be of any suitable shape and form, provided that is configured to releasably receive and hold the conductive membrane such that it extends at least partially over the electrodes in order to make contact with the electrodes. The support may be provided with retaining formations such as clips or straps (not shown) that are made of a non-conductive material and that extend from opposite sides of the support crosswise at least partially across the surface of the electrodes to hold the conductive membrane in place and ensure contact between the membrane and the electrodes.

In further embodiments of the invention, the support may be modified by providing it with a membrane frame or lid that cooperates with the support in a snap fit, or with the sliding member that cooperates with the support to allow for quick and easy exchange of the membrane.

The electrodes may be made of any suitably conductive material. In the embodiments described gold and copper electrodes were used. However, platinum electrodes are less reactive and may be able to provide more accurate resistance and rate of change of resistance readings upon molecular binding between the biological recognition component and the biomolecules of the sample. Copper is, however, the more cost-effective material for manufacturing the electrodes or terminal connections to the membrane.

A battery may be provided as a power source to supply a current to the circuit, and a voltage to the circuit. The battery may also power a controller, which is ideally a micro controller such as an Arduino micro controller consisting of a computer with suitable hardware and software installed thereon, which is connected to control circuitry and is configured to control the voltage measurement device and take readings from the device in order to calculate the resistance of the membrane. The device may further include wireless communication means, such as Bluetooth, in order to communicate the measurements or detection signals to a mobile or other device. These components can be used to create a compact and portable device for quick and easy use in the field.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. A device comprising:
an electrically conductive membrane comprising a biological recognition component selected to bind to a target biomolecule immobilized thereon, the membrane being connected to an electric circuit via electrodes, the membrane being mounted on a non-conducting support that releasably receives and holds the membrane such that the membrane contacts the electrodes;
a voltage source to provide a voltage within the electric circuit; and
a resistance monitoring device to monitor a resistance of the membrane as a selected volume of a fluid sample is delivered onto the membrane.

2. The device as claimed in claim 1, wherein the support defines a chamber that houses the membrane and wherein the electrodes extend into the chamber to contact the membrane housed therein.

3. The device as claimed in claim 1, wherein the support comprises an inlet for delivery of the selected volume of the fluid sample onto the membrane, the selected volume of the fluid sample being between 10 and 1000 µl.

4. The device as claimed in claim 1, wherein the membrane is made of inherently electrically conductive fibers or is made of polymer fibers coated with an electrically conductive coating.

5. The device as claimed in claim 1, wherein the membrane is made of polymer fibers coated with an electrically conductive coating, optionally comprising a dopant, and the electrically conductive coating is a polymeric coating selected from the group consisting of polypyrrole, polythiophene, polyaniline and polyacetylene.

6. The device as claimed in claim 1, wherein the biological recognition component is attached to the membrane by a cross-linking agent.

7. The device as claimed in claim 1, wherein the biological recognition component is an antigen for operatively binding to a target antibody or an antibody for operatively binding to a target antigen.

8. The device as claimed in claim 1, further comprising a controller that comprises hardware and software installed thereon and that is connected to the voltage source and the resistance monitoring device via control circuitry, the software, when executed by the hardware, causes the controller to issue machine-readable instructions to the voltage source to apply a voltage and to issue machine-readable instructions to the resistance monitoring device to take readings of the resistance across the membrane.

9. The device as claimed in claim 8, wherein the controller is connected to a signaling component via the control circuitry, and wherein the software, when executed by the hardware, causes the controller to issue instructions to the signaling component to signal a detection of the target biomolecule if a resistance is measured by the resistance monitoring device that is above a threshold resistance, wherein the threshold resistance is a resistance of the membrane without a fluid sample delivered onto the membrane.

10. The device as claimed in claim 8, wherein software, when executed by the hardware, causes the controller to process the readings of the resistance across the membrane to quantify an amount of the target biomolecule in the sample and assign a level of contamination or infection to the fluid sample.

11. The device as claimed in claim 8, wherein the controller has a user interface and display for displaying a signal, quantified amount of biomolecules and/or a level of contamination or infection.

12. The device as claimed in claim 8, wherein the controller is connected to a signaling component via the control circuitry, and wherein the software, when executed by the hardware, causes the controller to issue instructions to the signaling component to signal the detection of a target biomolecule if a resistance is measured by the resistance monitoring device that is above a threshold resistance which is a resistance of the membrane with a control fluid containing no biomolecules delivered onto the membrane.

13. The device as claimed in claim 8, wherein the controller is connected to a signaling component via the control circuitry, and wherein the software, when executed by the hardware, causes the controller to issue instructions to the signaling component to signal the detection of a target biomolecule if a resistance is measured by the resistance monitoring device that is above a threshold resistance which is a resistance of the membrane with a control fluid, containing biomolecules that the biological recognition component does not bind to, delivered onto the membrane.

14. The device as claimed in claim 1, wherein the resistance monitoring device is a voltage measurement device connected across the membrane and for the resistance of the membrane to be determined from a voltage drop measured across the membrane.

15. The device as claimed in claim 1, wherein the device is portable and battery-operated.

16. A method comprising:
delivering a selected volume of a fluid sample onto an electrically conductive membrane on which a biological recognition component that binds to a target biomolecule is immobilized, wherein the membrane comprises a biological recognition component selected to bind to a target biomolecule immobilized thereon, the membrane being connected to an electric circuit via electrodes, the membrane being mounted on a non-conducting support that releasably receives and holds the membrane such that the membrane contacts the electrodes;
monitoring a resistance of the membrane as the selected volume of the fluid sample is delivered onto the membrane; and
if the resistance is above a threshold resistance, signaling a detection of the target biomolecule.

17. The method of claim 16, wherein the threshold resistance is a resistance of the membrane without a fluid sample delivered onto the membrane.

18. The method of claim 16, wherein the threshold resistance is a resistance of the membrane with a control fluid containing no biomolecules delivered onto the membrane.

19. The method of claim 16, wherein the threshold resistance is a resistance of the membrane with a control fluid, containing biomolecules that the biological recognition component does not bind to, delivered onto the membrane.

* * * * *

UNITED STATES PATENT AND TRADEMARK OFFICE
CERTIFICATE OF CORRECTION

PATENT NO. : 10,302,637 B2
APPLICATION NO. : 15/352690
DATED : May 28, 2019
INVENTOR(S) : Viviers et al.

Page 1 of 1

It is certified that error appears in the above-identified patent and that said Letters Patent is hereby corrected as shown below:

On the Title Page

Item (56), Column 2, Other Publications, Line 2:
Delete "Microfthers" and insert --Microfibers--

Signed and Sealed this
Fifth Day of November, 2019

Andrei Iancu
*Director of the United States Patent and Trademark Office*